United States Patent [19]

Ward

[11] Patent Number: 4,707,389
[45] Date of Patent: Nov. 17, 1987

[54] MULTILAYER TUBE, ASSEMBLY AND METHOD

[75] Inventor: James R. Ward, Crystal Lake, Ill.

[73] Assignee: Baxter Travenol Laboratories, Inc., Deerfield, Ill.

[21] Appl. No.: 537,758

[22] Filed: Sep. 30, 1983

[51] Int. Cl.⁴ .............................................. D32B 7/02
[52] U.S. Cl. ..................................... 428/36; 428/518; 428/520; 428/522; 428/35; 383/904; 383/906
[58] Field of Search ................... 428/35, 36, 518, 520, 428/522; 383/904, 906

[56] References Cited

U.S. PATENT DOCUMENTS

| | | | |
|---|---|---|---|
| 4,327,726 | 5/1982 | Kwong et al. | 604/262 |
| 4,424,243 | 1/1984 | Nishmoto et al. | 428/36 |
| 4,465,487 | 8/1984 | Nakamura et al. | 428/35 |
| 4,501,780 | 2/1985 | Walters et al. | 428/520 |

FOREIGN PATENT DOCUMENTS

| | | | |
|---|---|---|---|
| 120957 | 7/1974 | Japan | 428/36 |
| 20043 | 11/1983 | Japan | 428/522 |
| 958 | 1/1985 | Japan | 428/522 |

*Primary Examiner*—Edith Buffalow
*Attorney, Agent, or Firm*—P. C. Flattery; R. M. Barrett; B. R. L. Price

[57] ABSTRACT

A multilayered tube (10) is provided that includes an outer layer (12) comprising ethylene-vinyl acetate for bonding to an ethylene-vinyl acetate material and an inner layer (14) comprising polyvinyl chloride for bonding to polyvinyl chloride material. A bonding layer (16) is provided between the outer and inner layers for bonding and preventing delamination of the outer and inner layers.

In another embodiment, a port and membrane tube assembly (18) is provided that includes the above-described multilayered tube and a polyvinyl chloride membrane tube bonded to the inner layer of the multilayered tube.

The multilayered tube or the port and membrane tube assembly can be bonded to an ethylene-vinyl acetate container which can be used to store various types of solutions useful in medical treatment.

8 Claims, 4 Drawing Figures

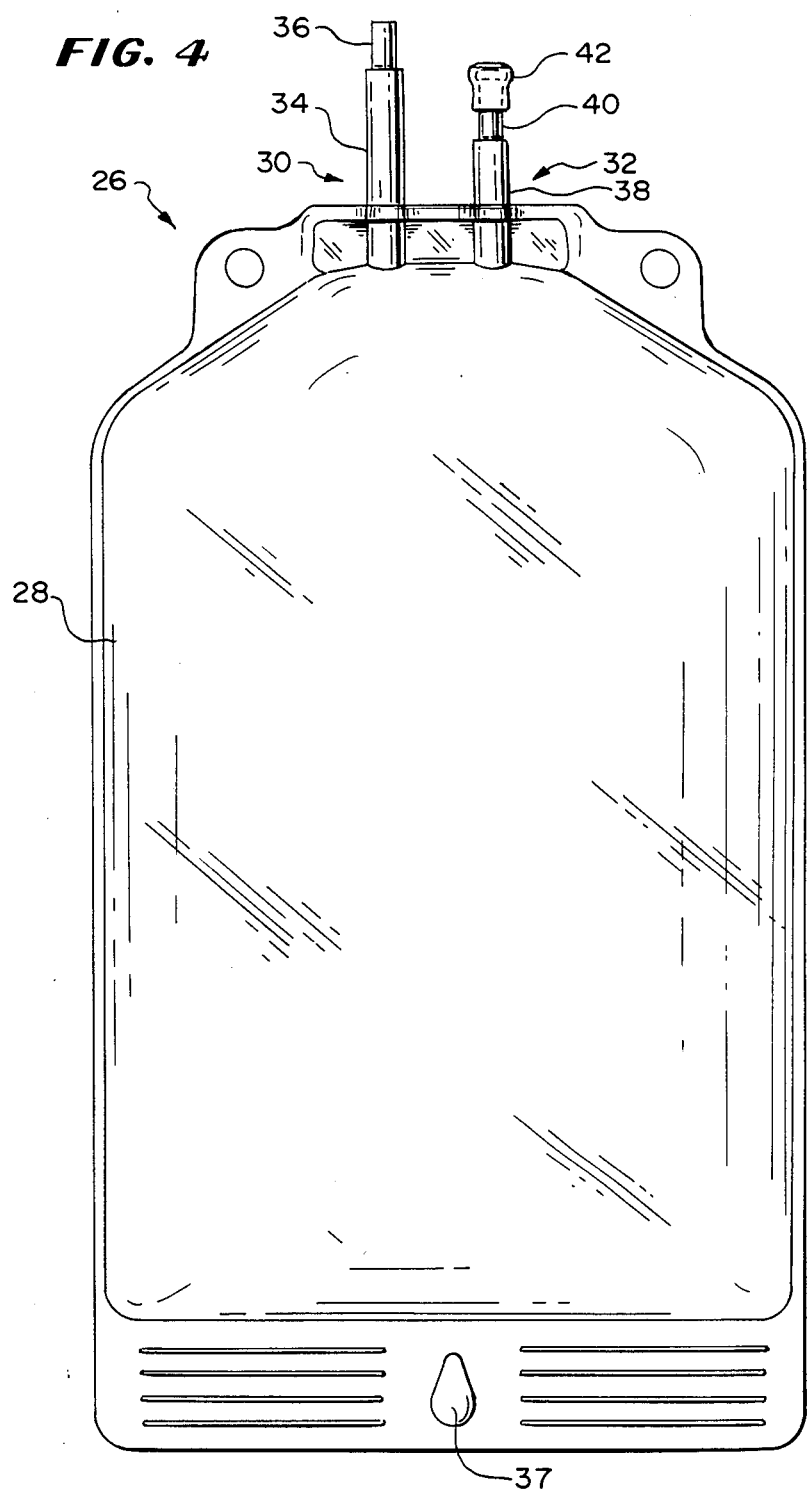

MULTILAYER TUBE, ASSEMBLY AND METHOD

FIELD OF THE INVENTION

This invention generally relates to port tubes and assemblies for use with containers. More particularly, the invention relates to co-extruded port tubes for medical grade ethylene-vinyl acetate copolymer containers.

BACKGROUND ART

In medical treatment therapy, individuals may require the intravenous administration of various types of fluids containing amino acids, dextrose, lipid emulsions and/or various types of vitamins and drugs. Types of storage containers and methods of administering such fluids to patients have been developed and are known in the art.

One known type of storage container is constructed of flexible, medical grade polyvinyl chloride (PVC). The container can be constructed of two sheets of PVC material, for example, and bonded together along the periphery to form a container bag. Access to the bag is provided, for example, by a port tube communicating with the interior of the container and sealed between the two sheets of the container. A membrane tube having an inner pierceable membrane can be secured by solvent bonding, for example, to the interior of the end of the port tube opposite the end that communicates with the interior of the container. Access to the container can be achieved by inserting a spike through the inner pierceable membrane of the membrane tube. The spike is attached to tubing which can be directed into a patient, for example.

Polyvinyl chloride material is currently the best type of material to be used for the membrane tube, including the inner pierceable membrane. Use of PVC material for the membrane allows relatively easy insertion and withdrawal of the spike from the membrane and provides a good seal between the membrane and the spike.

For storing materials such as amino acids, dextrose solutions, lipid emulsions, fat soluble vitamins, and various types of drugs and medications, such as nitroglycerin, an improved container material has been developed. The improved container material is ethylene-vinyl acetate (EVA) and exhibits several advantages over flexible PVC material. Containers made from ethylene-vinyl acetate material exhibit less leaching of material into the fluid being stored in the container. Another advantage is that certain materials which may be stored in the container will be absorbed to a lesser degree by ethylene-vinyl acetate material than PVC material. Thus, for some applications, storage bags made of ethylene-vinyl acetate material are preferred to PVC bags.

In order to maximize the usefulness of EVA containers, a port tube and port and membrane tube assembly specifically for use with EVA containers is needed. Various types of port tubes and membrane tubes have been utilized with EVA containers but none has been completely acceptable. For example, an EVA port tube has been utilized with an EVA membrane tube. Use of an EVA port tube with an EVA container results in a good bond which can be formed by using radio frequency (R.F.) energy. However, it is not practical to R.F. bond the EVA membrane tube to the EVA port tube since the membrane could be damaged by R.F. energy thereby possibly affecting the sterility of the container. The EVA membrane tube can be cemented into the EVA port tube with a cement comprising about 90% toluene and 10% of EVA. However, this has disadvantages since the adhesive must be heated and agitated for several hours to produce a homogeneous cement. Further, the cement requires a minimum drying time of twenty-four hours before further processing or testing.

Use of an EVA membrane tube is not completely acceptable for other reasons. Insertion of a spike through the EVA membrane is relatively difficult. Further, removal of the spike generally does not occur without separating the membrane tube from the port tube due to the relatively weak bond strength provided by cementing the EVA membrane tube into the EVA port tube and the adherence of the EVA membrane to the spike. When removal of the spike causes separation of the membrane tube from the port tube, the spike and its associated tubing and connections must be discarded since a suitable method of aseptically removing the EVA membrane tube from the spike is not available. Since one patient may require as many as four bag or container changes in a twenty-four hour period, this results in the use of a large number of spikes and associated tubing and connections.

The use of a PVC port tube with a PVC membrane tube or an EVA port tube with a PVC membrane tube is not feasible with an EVA container since a suitable method of bonding the PVC to EVA is not available. For example, a suitable bond between EVA and PVC is not obtained with R.F. energy due to the incompatibilities of PVC and EVA.

Thus, a need exists for a suitable port tube and port and membrane tube assembly for use in connection with a flexible EVA container and a ported EVA container that is suitable for medical uses that overcome the foregoing disadvantages, including difficulty in spike removal and separation of the membrane tube from the port tube.

DISCLOSURE OF THE INVENTION

In accordance with the present invention, an improved port tube is provided that is suitable for use with EVA containers, such as flexible EVA bags and which allows the use of a PVC membrane tube to be adequately secured within the port tube to allow spike removal without separating the membrane tube from the port tube. The port tube can be secured to the EVA container by R.F. energy.

The tube in accordance with the invention is a multilayered tube having an outer layer comprising ethylene-vinyl acetate and an inner layer comprising polyvinyl chloride. The inner and outer layers are bonded together by a bonding layer of any suitable material between the inner and outer layers. The bonding layer material can be a coextrudable adhesive resin and should be a suitable adhesive for bonding EVA and PVC. One such bonding layer material is a tripolymer composed of ethylene, vinyl acetate and acrylic based material. The tube can be cylindrical or any desired shape.

The EVA layer of the multilayered port tube should be thick enough to allow bonding of the port tube to an EVA bag container by R.F. energy. The thickness of the PVC layer should be thick enough to allow solvent bonding of a PVC membrane tube to the inner surface of the multilayered port tube. The thickness of the bonding layer is sufficient to provide a good bond between the EVA and PVC layers. Generally, the thickness of the bonding layer will be substantially less than the thickness of each of the EVA and PVC layers. The overall thickness of the tube should be such that the tube is self-supporting and the desired physical integrity and strength is provided.

In accordance with another aspect of the invention, a port and membrane tube assembly is provided that includes a multilayered port tube having an outer (EVA) layer, a bonding layer and an inner (PVC) layer as previously described. The membrane tube comprises PVC material and is bonded to the surface of the inner or PVC layer of the multilayered port tube. One suitable method of bonding the PVC membrane tube to the multilayered port tube is by solvent bonding.

In accordance with another aspect of the invention, a ported container is provided that includes a flexible EVA container or bag and a multilayered port tube as previously described. The port tube communicates with the interior of the container and the outer (EVA) layer is bonded to the EVA container. In addition, a PVC membrane tube can be bonded to the inner layer of the multilayered port tube opposite the end of the port tube that communicates with the EVA con- tainer.

In accordance with another aspect of the invention, a method of making a port and membrane tube assembly is provided that includes providing a multilayered port tube of the type described and a PVC membrane tube and bonding the PVC membrane tube to the inner (PVC) layer of the multilayered port tube. One method of making the multilayered port tube is by coextruding the materials of the outer, bonding and inner layers.

BRIEF DESCRIPTION OF THE DRAWINGS

The present invention can be more completely understood by reference to the accompanying drawings in which:

FIG. 4 is an elevation view of a ported container including a multilayered port tube and membrane tube assembly in accordance with the present invention.

DETAILED DESCRIPTION

Figure 1:
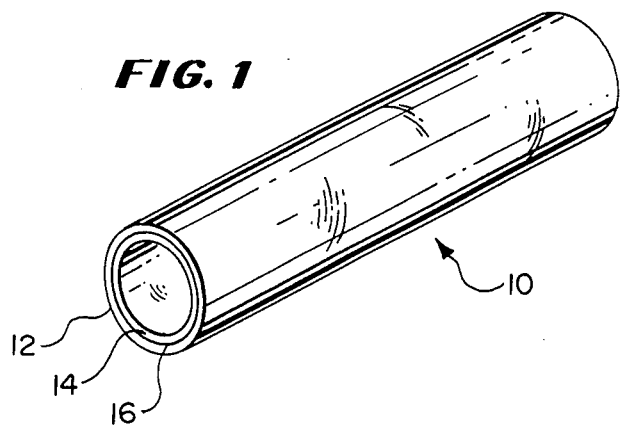
FIG. 1 is a perspective view of a multilayered port tube in accordance with the present invention.

Referring to the drawings generally, and in particular to FIG. 1, there is illustrated a multilayered port tube 10 in accordance with the present invention. Multilayered port tube 10 is cylindrical in shape and is made up of three coaxial layers. An outer layer 12 comprises ethylene-vinyl acetate material, outer layer 12 providing a bonding surface for bonding to ethylene-vinyl chloride material, such as a flexible container. Inner layer 14 forms the interior of multilayered port tube 10 and comprises polyvinyl chloride material. Inner layer 14 provides a bonding surface for polyvinyl chloride material, such as a membrane tube which is inserted into one end of multilayered port tube 10 and bonded to inner layer 14 as hereinafter described with reference to FIG. 3.

Experiments have shown that a bonding layer is required to prevent delamination between outer layer 12 and inner layer 14. Without a bonding layer, delamination often begins to occur after exposure to temperatures of about 140° F. for five days. Since temperatures in this range can be encountered in transporting the devices, such devices would not be practical for commercial use.

It has been discovered that a layer of material that is an ethylene based polymer containing vinyl acetate and an acrylic based material provides a good bond between the layers of ethylene-vinyl acetate and polyvinyl chloride, with no delamination after extended periods of exposure at about 140° F.

Figure 2:
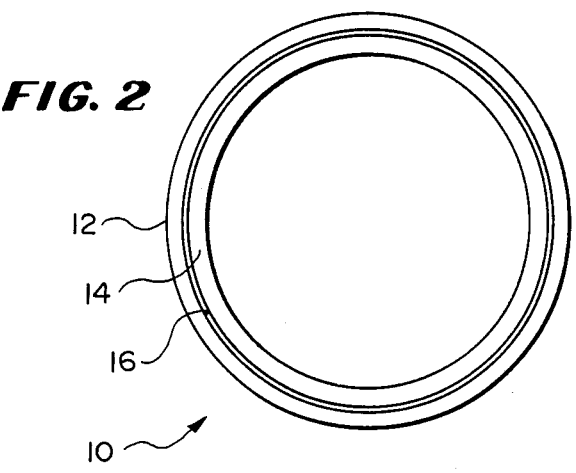
FIG. 2 is a greatly enlarged end view of a multilayered port tube in accordance with the present invention.

As shown in FIG. 1, and in greater detail in FIG. 2, a bonding layer 16 is provided between outer layer 12 and inner layer 14 that is a mixture of ethylene-vinyl acetate and low density polyethylene. Bonding layer 16 can be relatively thin compared with the thicknesses of outer layer 12 and inner layer 14. For example, in one specific embodiment, a multilayered port tube is provided having a thickness of the outer (ethylene-vinyl acetate) layer of about 0.015 inches, a thickness of the inner (polyvinyl chloride) layer of about 0.015 inches and a bonding layer thickness of about 0.002 inches, the multilayered port tube having an interior diameter of about 0.245 inches.

Generally, outer layer 12 should be constructed of medical grade ethylene-vinyl acetate. An especially preferred type of ethylene-vinyl acetate is available from U.S. Industrial Chemicals Co. of New York, N.Y., marketed under the trademark "Ultrathene®", product designation number UE-634-00. Ultrathene® UE-634-00 is an ethylene-vinyl acetate polymer having a vinyl acetate content of about 28% by weight of the polymer. Other Ultrathene® EVA polymers have different amounts of vinyl acetate, between about 10 and 32%, and can also be useful.

The inner layer, which comprises polyvinyl chloride, preferably includes a suitable plasticizer and heat stabilization system.

The polyvinyl chloride resin can be any suitable type. Those types of PVC resins which relatively easily absorb the plasticizer are preferred. Especially suitable resins are those known as "blotter" resins. One such preferred resin is marketed by B. F. Goodrich Chemical Co. under the trade designation "GEON." Another suitable PVC resin is marketed by Diamond Shamrock under the trade designation "PVC500."

Any suitable plasticizer can be used. One especially suitable plasticizer is tri (2-ethylhexyl) trimellitate, which is commercially available. One source is the Hatco Chemical Corp. marketing the plasticizer under the trade designation "Hatcol 200."

The heat stabilization system can include an epoxidized vegetable oil that is a suitable heat stabilizer for polyvinyl chloride and is usually present in an amount greater than about 3% by weight. The heat stabilization system may also include a small amount of a metal soap, such as calcium and/or zinc stearate.

The material for providing a bonding layer for the outer EVA and inner PVC layers can be any suitable material which prevents delamination of the layers at exposure to temperatures of up to about 130° F. to 140° F. for extended periods of time. One suitable material for the bonding layer is an ethylene based polymer containing vinyl acetate and an acrylic based material. The material present in the bonding layer can be any suitable type and amount which achieves the desired bonding effect, or stated otherwise, prevents delamination of the EVA and PVC layers under conditions which can be normally encountered in shipping, storage and use of the multilayered port tube. The maximum temperature to which the multilayered port tube is expected to normally encounter is about 140° F., and more typically, about 130° F. Preferably, the material of the bonding layer should be of the type that can be extruded, such as a coextrudable adhesive resin. One such material that is especially suitable for the bonding layer is a material marketed by E. I. DuPont de Nemours under the trade designation "CXA-1123." "CXA-1123" is a proprietary polymer in pelletized form that is ethylene based and contains vinyl acetate and an acrylic based material. A similar type of polymer which is also suitable is DuPont's "CXA-1124."

Any suitable method for making a multilayered port tube in accordance with the invention can be employed. One especially suitable method is extrusion. The three layers that make up the multilayered port tube can be coextruded by utilizing three extruders which simultaneously feed through a single die to produce the coextruded multilayered port tube.

Figure 3:
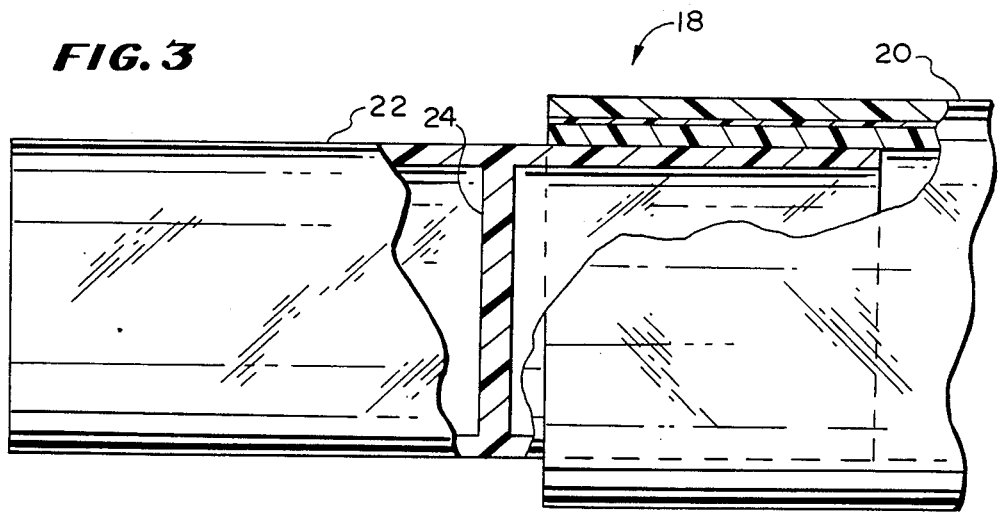
FIG. 3 is a side, partially sectional view of a multilayered port tube and membrane tube assembly in accordance with the present invention.

Referring now to FIG. 3, there is illustrated a partially sectional side view of a port and membrane tube assembly 18 in accordance with the present invention. Port and membrane tube assembly 18 includes a multilayered port tube 20 and a membrane tube 22. Multilayered port tube 20 is similar to multilayered port tube 10 and includes an outer layer of ethylene-vinyl acetate material, a bonding layer that is an ethylene based polymer containing vinyl acetate and an acrylic based material and an inner layer of polyvinyl chloride material.

Membrane tube 22 is constructed of polyvinyl chloride material and can be a composition similar to that employed for the inner layer of multilayered port tube 20. Membrane tube 22 includes a membrane 24 which provides a seal across the interior of membrane tube 22. Membrane 24 is usually constructed of the same material as membrane tube 22.

Membrane tube 22 is dimensioned to be inserted into one end of multilayered port tube 20 in frictional engagement. The inserted end of membrane tube 22 is bonded to the inner PVC layer of multilayered port tube 20 by any suitable method that provides sufficient bond strength. The bond strength should be sufficient so that when a spike that has been inserted through membrane 24 is removed, the bond between membrane tube 22 and multilayered port tube 20 remains intact. One especially suitable bond is a solvent bond formed between the inner PVC layer of multilayered port tube 20 and membrane tube 22 with cyclohexanone.

Referring now to FIG. 4, there is illustrated a ported container 26 that includes a bag portion 28 and ports 30 and 32. Port 30 is a port and membrane tube assembly including a multilayered port tube 34 and a membrane tube 36. Multilayered port tube 34 and membrane tube 36 are similar to multilayered port tube 20 and membrane tube 22 of port and membrane tube assembly 18, previously described. Container 26 may be filled with a desired fluid (not shown) and is especially suitable for storing fluids containing amino acids, dextrose, and lipid emulsions, for example.

Bag portion 28 of ported container 26 is formed by attaching two overlapping sheets of ethylene-vinyl acetate material along their periphery. Such attachment can be made by R.F. energy. Bag portion 28 includes a hanger 37.

Port 32 is provided for injection of a desired material into bag portion 28. Port 32 includes a multilayered port tube 38, similar to multilayered port tube 20 and a membrane tube 40, which is similar to membrane tube 22 with the exception that the end of membrane tube 40 opposite the end which is secured within multilayered port tube 38 has a lip thereon which assists in retaining a rubber plug 42 which is inserted into the end of membrane tube 40. Rubber plug 42 includes a cylindrical flap portion which can be stretched over the end and lip of membrane tube 40 to help maintain rubber plug 42 therein. When an injection is made into bag portion 28, the needle portion of a syringe penetrates through rubber plug 42 and the membrane of membrane tube 40 to communicate with the interior of ported container 26. The needle can be withdrawn from the membrane of membrane tube 40 and from rubber plug 42 when desired, such as after an injection has been made. Rubber plug 42 provides a seal after the needle is withdrawn.

Ports 30 and 32 are attached to bag portion 28 of ported container 26 by inserting one end of each of multilayered port tubes 34 and 38 between the two sheets of the EVA material of bag portion 28. A seal is formed between the outer layer of each of multilayered port tubes 34 and 38 and the two sheets of bag portion 28 by any suitable method, such as, for example, R.F. energy. While ported container 26 includes two ports, any desired number of ports can be provided.

EXAMPLE 1

A port tube not in accordance with the invention was made by coextruding a tube to provide an outer layer of ethylene-vinyl acetate and an inner layer of polyvinyl chloride. The thickness of each of the inner and outer layers was about 0.015 inches. The coextruded port tube was subjected to a temperature of about 140° F. for about five days. After this period of time, the inner PVC layer had begun to delaminate from the outer EVA layer.

EXAMPLE 2

A multilayered port tube in accordance with the present invention was made by coextrusion to provide a tube comprising an outer EVA layer, a center bonding layer of DuPont's CXA-1123 and an inner layer of a PVC composition.

The EVA and PVC compositions were the same as used for the port tube of Example 1. The EVA was Ultrathene ® UE-634-00. The polyvinyl chloride composition contained about 60% by weight of PVC500, about 30% by weight Hatcol 200, about 9% by weight of an epoxidized vegetable oil from the Unitech Co. of the trade designation Epoxol and less than about 1% by weight of a metal soap heat stabilizer material.

The foregoing materials were coextruded utilizing three one-inch extruders simultaneously feeding through a single die to produce the coextruded multilayered port tube having an outer EVA layer of about 0.015 inches in thickness, a bonding layer of CXA-1123 of about 0.002 inches in thickness and an inner PVC layer of about 0.015 inches in thickness.

The multilayered port tube was subjected to a temperature of about 140° F. and held at this temperature for a period of sixty-four days. After this period of time, no delamination of the tube layers was evident.

Whereas the present invention has been described with respect to specific embodiments thereof, it will be understood that various changes and modifications will be suggested to one skilled in the art and it is intended that the invention encompass such changes and modifications as fall within the scope of the appended claims.

I claim:

1. A multilayered tube securable to a container constructed from ethylene-vinyl acetate the multilayered tube comprising an outer layer comprising ethylene-vinyl acetate for bonding the multilayered tube to the ethylene-vinyl acetate container, an inner layer comprising polyvinyl chloride for bonding to polyvinyl chloride material and a bonding layer between said outer and inner layers for bonding and preventing delamination of said inner and outer layers.

2. The multilayered tube of claim 1 wherein said outer and inner layers are bonded together by material comprising a coextrudable resin that is an adhesive for the ethylene-vinyl acetate and the polyvinyl chloride.

3. The multilayered tube of claim 1 wherein said bonding layer is relatively thin compared to said inner and outer layers.

4. The multilayered tube of claim 1 formed by coextruding the materials which form said outer, bonding and inner layers.

5. The multilayered tube of claim 1 wherein said layers are coaxial and cylindrical.

6. The multilayered tube of claim 1 wherein said ethylene-vinyl acetate of said outer layer contains from about 10% to about 32% vinyl acetate by weight.

7. The multilayered tube of claim 1 wherein said ethylene-vinyl acetate of said outer layer contains about 28% vinyl acetate by weight.

8. The multilayered tube of claim 1 wherein the bonding layer is chosen from the group consisting of ethylene-vinyl acetate and low density polyethylene, and ethylene copolymer containing vinyl acetate and an acrylic based material.

* * * * *